United States Patent [19]

Pudenz

[11] 4,099,315

[45] Jul. 11, 1978

[54] PROCESS FOR FIXING THE CENTER OF ROTATION BETWEEN THE LEGS OF TWO-LEGGED DEVICES

[75] Inventor: Alfred Pudenz, Wanfried, Fed. Rep. of Germany

[73] Assignee: B. Braun Instruments, South San Francisco, Calif.

[21] Appl. No.: 772,577

[22] Filed: Feb. 28, 1977

[30] Foreign Application Priority Data

Mar. 19, 1976 [DE] Fed. Rep. of Germany ....... 2611646

[51] Int. Cl.² ............................................. B23P 11/00
[52] U.S. Cl. .......................................... 29/434; 81/416
[58] Field of Search ............................ 81/416; 29/434; 76/101 R, 101 D

[56] References Cited

U.S. PATENT DOCUMENTS 2,305,156  12/1942  Grubel ................................... 81/416

FOREIGN PATENT DOCUMENTS 604,813  5/1960  Italy ......................................... 81/416

Primary Examiner—Lowell A. Larson
Attorney, Agent, or Firm—Curtis, Morris & Safford

[57] ABSTRACT

The pivotal connection between the legs of a two-legged device, such as a surgical forceps, having a first leg including a mounting passage formed therein and a second leg which is inserted in the mounting passage is formed by expanding the mounting passage of said first leg by heating at least the portion of that leg having the passage therein to a predetermined temperature; inserting a pivot member in a pivot opening in the second leg; inserting said second leg through the mounting passage of the first leg until the pivot member is within the confines of the mounting passage and then compressing the portion of the first leg having the mounting passage therein towards the other leg to engage the pivot member against the internal sides of the passage.

6 Claims, 8 Drawing Figures

FIG. 2 FIG. 1
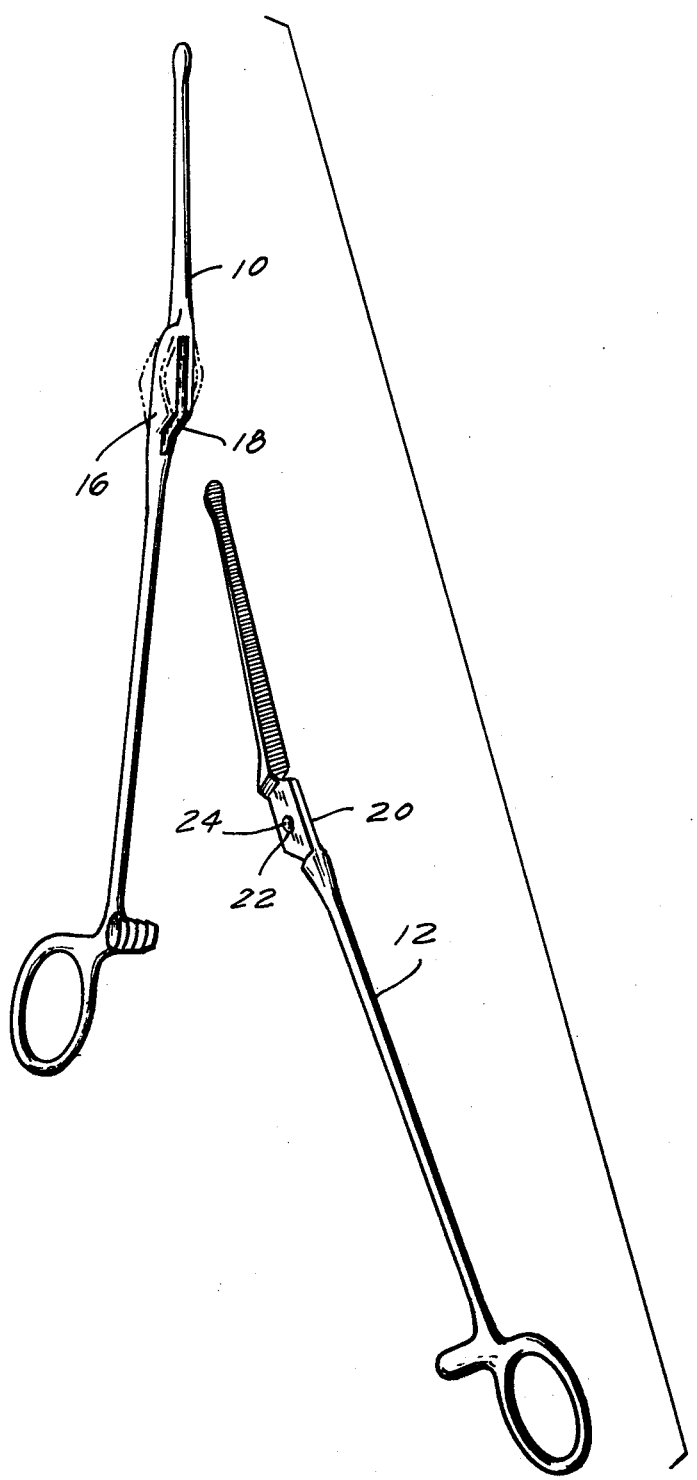

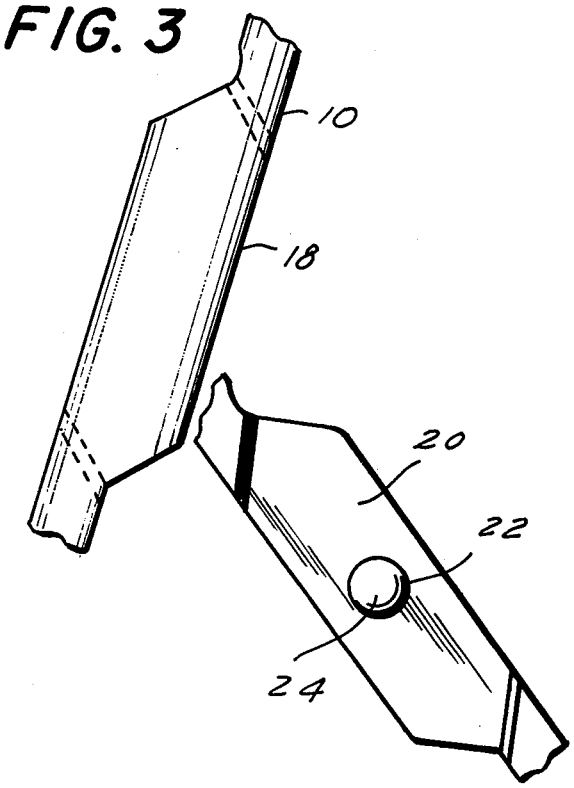
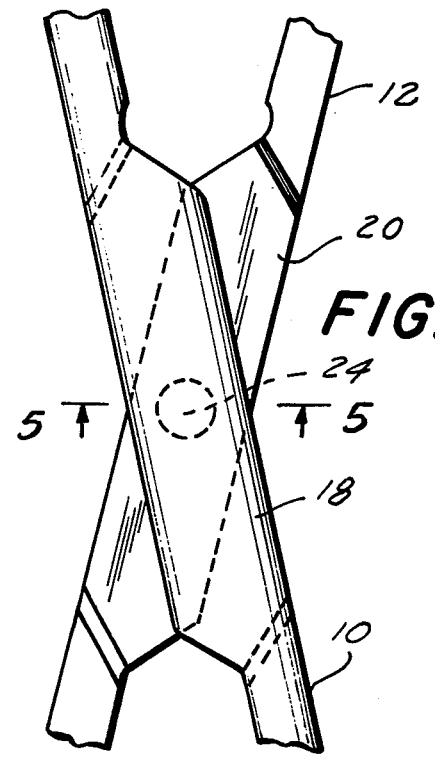
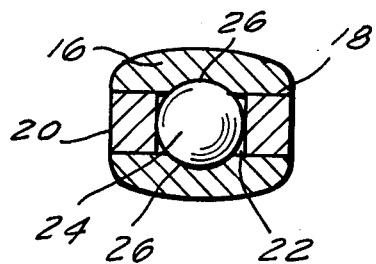
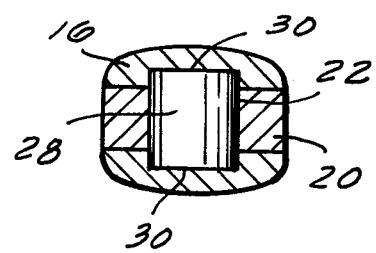
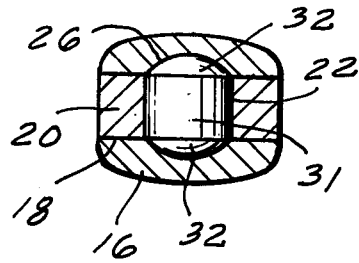
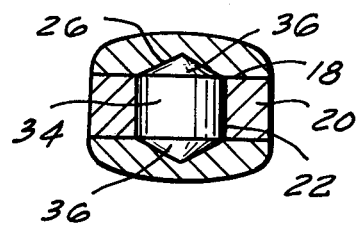

PROCESS FOR FIXING THE CENTER OF ROTATION BETWEEN THE LEGS OF TWO-LEGGED DEVICES

The present invention relates to a process for forming the center of rotation between the legs of two-legged devices and, more particularly, to a method of forming an improved pivotal connection in surgical devices.

Two-legged surgical instruments, for example, forceps, clips, suture-needle holders, blocking means and scissors, typically have pass-through openings or mounting passages in one leg which receives the other leg of the device. In one form of such devices one of the legs has a parallelogram-like pass-through opening milled out in the zone adjacent the center of rotation, or pivotal connection between the legs. The other leg of the device is dimensioned to be passed through the milled out passage in the first leg, and its side surfaces are milled in a parallelogram-like manner on both sides in the zone of the center of rotation to be closely received in the passage. To form the pivotal connection between the legs there has been used hitherto a rivet or pin extending through a bore passing through both leg parts. In order to pass the leg which is milled off on both sides in the zone of its center of rotation through the milled out through opening or mounting passage in the first leg, the first leg is expanded in the zone of the through opening or mounting passage by heating to the annealing temperature of the material of which it is formed; this is usually a temperature of about 900° to 1000° C. After the milled off leg has been passed through the mounting passage the first leg is compressed again in a predetermined configuration. Subsequently, the center of rotation between the two legs is fixed and formed by riveting the legs together.

This method of forming the center of rotation between the legs of two-legged devices has the drawback that the motion of the legs during opening and closing is not uniform, and thus the function of the instrument is impaired. In addition this method of assembly may cause cracking in the metal surface of the instrument which leads to a destruction of the passive layer or protective coating thereon, and, hence to corrosion of the device. Moreover, at the point of riveting tension stresses are produced in the material which often leads to cracks that make the instruments useless; and upon use of the instrument the rivet slackens, which also makes the instrument useless.

Accordingly, it is an object of the present invention to provide an improved process for forming the center of rotation between the legs of two-legged devices, by means of which the drawbacks described above are avoided.

Another object of the present invention is to pivotally connect the legs of a surgical instrument by a process which is relatively simple to perform and inexpensive in operation.

In accordance with an aspect of the present invention a pivotal connection is formed between the legs of a two-legged device in which one of the legs has a mounting passage formed therein and the other of the legs is inserted in that passage for pivotal connection to the first leg. To form the pivotal connection the mounting or through passage in the first leg is expanded by heating at least that portion of the leg to a predetermined annealing temperature of about 900° to 1000° C. A pivot member, such as a metal sphere, is mounted in the other or second of the legs at the point forming the pivotal connection therebetween, with the pivot member extending beyond the sides of the leg. The second leg is then inserted into the expanded mounting passage until the pivot member is within the confines of the passage. With the second leg thus positioned the mounting passage of the first leg is compressed towards the second leg to firmly engage the pivot member against the inner sides of the passage.

The above, and other objects, features and advantages of this invention will be apparent in the following detailed description of illustrative embodiments thereof, which is to be read in connection with the accompanying drawings, wherein:

FIG. 1 is a perspective view of a surgical instrument whose legs are pivotally connected by the method of the present invention;

FIG. 2 is an exploded perspective view of the instrument shown in FIG. 1;

FIG. 3 is an enlarged, partial side view showing insertion of one of the instrument legs into the other;

FIG. 4 is an enlarged partial side view showing the pivotal connection between the legs;

FIG. 5 is a sectional view taken along line 5—5 of FIG. 4; and

FIGS. 6, 7 and 8 are sectional views similar to FIG. 5 of other embodiments of the invention.

Referring now to the drawings, and initially to FIGS. 1–3 thereof, the method of the present invention is used to form a pivotal connection between the first and second legs 10, 12 of a two legged surgical instrument 14 or the like. In the illustrative embodiment of the invention, a forceps is shown, but the invention is adapted to be used with other instruments, as described above.

The first leg part 10 of instrument 14 has a central portion 16 in which a pass-through opening or mounting passage 18 is formed, e.g. by milling. This passage has a parallelogram like configuration in the conventional manner. The second leg 12 has a thin central portion 20, which is formed by milling the sides of the leg to provide a parallelogram-like configuration which is generally complementary to passage 18 so that legs 10, 12 match or mate with one another when leg 12 is passed through the passage in leg 10, as described hereinafter.

Leg part 12 has a milled out central circular opening 22 in its central portion 20 which is adapted to receive a metal pivot member, e.g. a metal ball 24 in a tight frictional engagement. The metal ball has a diameter which is greater than the width of central portion 20 of leg 12 so that it extends beyond this leg to form the pivotal connection or center of rotation between the legs in the finished instrument, as shown in FIGS. 4 and 5.

According to the method of the present invention, in order to pass leg 12 through the milled out parallelogram-like opening or mounting passage 18 in leg 10, the opening 18 is expanded (as shown in dotted lines in FIG. 2) by heating at least the portion of leg 10 adjacent the opening to the annealing temperature of the material of which the leg is formed. These instruments are typically formed of conventional metal materials, e.g. chromium steel, having annealing temperatures of about 900° to 100° C. Expansion of passage 10 may be the result of heating above, but if desired or necessary the side walls of the passage may be generally spread apart in any convenient manner. Leg 12 is then passed through the expanded opening 18 in leg 10 up to a predetermined position wherein the thin portion 20 of leg 12 is within the opening or passage 18. Prior to insertion of leg 12 in leg 10 metal ball 24 is placed in the circular opening 22 formed in the thin portion 20 of leg 12. After leg 12 is inserted in passage 10 so that the ball 24 is located within the confines of passage 18, leg 10 is compressed at the expanded point of the leg adjacent passage 18 in an adjustable press or the like until a predetermined seat is formed between the inner side surfaces of the side walls of passage 18 and the protruding surfaces of ball 24. This can be done while the walls of leg 10 are still hot from the prior heating step, or auxiliary heating can be performed if necessary. Due to the pressure of the side walls of passage 18 on metal ball 24, spherical segment-like depressions 26 are pressed into the internal walls of passage 18 which hold the ball in passage 18 and thus retain leg 12 in leg 10 (see FIG. 5). As a result the pivotal connection and center of rotation between the legs of the device is fixed. The ball 24 is fixed tightly in opening 22 but can rotate in depression 26.

As a result of this type of fixation of the center of rotation, the device is subject to very low abrasion in the pivot point, even if it is constantly used. Moreover points of pressure or friction do not occur, and little if any tension stresses are created in leg 12. Thus the fixation of the center of rotation according to the invention insures a soft and easy pivotal motion of the legs of the device.

The size of the ball forming the center of rotation depends on the dimensions and on the kind of use of the device, as well as on the strain to be expected.

In lieu of using the metal ball 24 to form the pivot point and pivot connection between legs 10 and 12 other forms of pivotal connecting members may be used. Thus, as seen in FIG. 6 a cylindrical rod 28 having a length greater than the width of leg 12 can be used so that its flat ends 30 extend beyond the sides of the thin central portion 20 of leg 12. Likewise, as seen in FIG. 7 a cylindrical rod 31 whose exposed ends 32 are generally semispherical can be mounted in the opening 22 of leg 12. And, as seen in FIG. 8 a rod 34 can be used having conically shaped end portions 36. In each case the protruding ends of the rods form complementary depressions 26 in the internal side surface of passage 18 when the sides of leg 10 are compressed towards leg 12 to capture and pivotally hold the ends of the rod and form the pivotal connection between legs 10 and 12.

Although illustrative embodiments of the invention have been described herein in connection with the accompanying drawings, it is to be understood that the invention is not limited to those precise embodiments and that various changes and modifications may be effected therein by one skilled in the art without departing from the scope or spirit of this invention.

What is claimed is:

1. The method of forming a pivotal connection between the legs of a two-legged device in which one of the legs has a mounting passage formed therein and the other of the legs is inserted in said passage and has a pivot opening formed therein; said method comprising the steps of expanding said mounting passage by heating at least the portion of the leg having said passage therein to a temperature of about 900° to 1000° C; inserting a pivot member having opposed spherical surfaces in the pivot opening of the other of said legs; inserting said other of said legs through said mounting passage until said pivot member is within the confines of said passage; and compressing the portion of said leg having the mounting passage therein adjacent said mounting passage towards said other leg to engage said opposed spherical surfaces of said pivot member against the inner sides of said passage.

2. The method as defined in claim 1 wherein said compressing step is performed while the leg having said passage therein is subjected to heat.

3. The method as defined in claim 2 wherein said step of inserting a pivot member comprises the step of inserting a spherical ball in said opening, having a diameter greater than the width of the leg in which it is inserted.

4. The method as defined in claim 2 wherein said step of inserting a pivot member comprises the step of inserting a rod in said opening having semi-spherical end portions and a length greater than the width of the leg in which it is inserted.

5. The method of forming a pivotal connection between the legs of a two-legged device in which one of the legs has a mounting passage formed therein and the other of the legs is inserted in said passage and has a pivot opening formed therein; said method comprising the steps of expanding said mounting passage by heating at least the portion of the leg having said passage therein to a temperature of about 900° C to 1000° C; inserting a pivot member having conically shaped end portions and a length greater than the width of the leg in which it is inserted in the pivot opening of the other of said leg; inserting said other of said leg through said mounting passage until said pivot member is within the confines of said passage; and compressing the portion of said leg having the mounting passage therein adjacent said mounting passage towards said other leg to engage said opposed conically shaped end portions of the pivot member against the inner sides of the passage.

6. The method as defined in claim 5 wherein said compressing step is performed while the leg having said passage therein is subjected to heat.

* * * * *